US00PP34161P2

(12) United States Plant Patent
McGinnis

(10) Patent No.: US PP34,161 P2
(45) Date of Patent: Apr. 26, 2022

(54) BLACK CURRANT PLANT NAMED 'NICOLA'

(50) Latin Name: ***Ribes nigrum* L.**
Varietal Denomination: Stikine

(71) Applicant: McGinnis Berry Crops Limited, Victoria (CA)

(72) Inventor: Richard McGinnis, Victoria (CA)

(73) Assignee: McGinnis Berry Crops Limited, Victoria (CA)

( * ) Notice: Subject to any disclaimer, the term of this patent is extended or adjusted under 35 U.S.C. 154(b) by 0 days.

(21) Appl. No.: 16/952,380

(22) Filed: Nov. 19, 2020

(51) Int. Cl.
*A01H 5/08* (2018.01)
*A01H 6/00* (2018.01)

(52) U.S. Cl.
USPC ..... Plt./156
CPC ..... *A01H 6/00* (2018.05); *A01H 5/08* (2013.01)

(58) Field of Classification Search
USPC ..... Plt./156
CPC ..... A01H 6/00
See application file for complete search history.

(56) References Cited

PUBLICATIONS

UPOV hit on Blackcurrant plant named, 'Nicola', CA PBR 19-10048, filed Nov. 25, 2019.*
UPOV hit on Black Currant plant named, 'Nicola', CA PBT 19-10048, filed Nov. 25, 2019.*

* cited by examiner

*Primary Examiner* — Anne Marie Grunberg
(74) *Attorney, Agent, or Firm* — Gearhart Law LLC; David Postolski

(57) ABSTRACT

A new and distinct cultivar of black currant plant (i.e. *Ribes nigrum* L.) is provided. Appealing flavor, long upright shoots, multiple racemes per bud, large fruits size and frost hardiness characterize the invention. The mid-season variety is ideal for North American markets due to the flavor, frost hardiness, high yields.

16 Drawing Sheets

Genus and species: A new and distinct cultivar of black currant plant (i.e. *Ribes nigrum* L.) is provided.

Variety denomination: The variety denomination is 'Nicola'.

BACKGROUND OF THE EMBODIMENTS

The new black currant plant (*Ribes nigrum* L.) cultivar, the invention, was created as part of the planned cross-breeding program beginning in 1998 in Courtenay, British Columbia, Canada. The new cross was completed in 2004 and selected for further field trials in 2008. The female (seed) parent used was 'Orlovskaya Serenada' (Minaj Shmyrev x Ershistaya) and the male (pollen) parent used was 'Titania' (Altaskaya Dessertnaya x [Consort x Kayaanin]), defined as 'Orlovskaya Serenada' x 'Titania'. 'Titania' is the subject of a U.S. Plant Pat. No. 11,439 granted Jul. 11, 2000. The patent status of 'Orlovskaya Serenada' is unknown since we do not speak Russian and cannot read search results on the internet although it is very likely that it is the subject of plant breeder's rights as it is a fairy recent release from the Orel breeding program.

'Nicola' is the product of a 2004 cross between 'Orlovskaya Serenada' as seed parent and 'Titania' as pollen parent. It was necessary to time the flowering as 'Orlovskaya' flowers 7-10 prior to Titania. We used a cooler to delay flowering in 'Orlovskaya Serenada'.

The crosses were made in a greenhouse to avoid losses due to frost. Pollen was extracted from anthers, using forceps. The anthers were placed under a heat lamp overnight. After removing the anthers from the seed parent with forceps, and with a separate set of forceps and with the aid of a magnifying visor, pollen was applied to each pistil. The pollinated flowers were covered with a bag for two weeks.

Seeds were collected from the pollinated flowers and stored in a cool place until they were planted in seed trays. The seeds were germinated in the greenhouse. Seedlings were screened for symptoms of White pine blister rust before selection. The plants were grown out for two years. Each year each plant was examined for symptoms of white pine blister rust. In 2020, each plant was evaluated for yield potential, growth habit, resistance to powdery mildew fruit size.

Trials were replicated in the following locations in Canada:

Courtenay, British Columbia
West Saanich, British Columbia
Chilliwack, British Columbia Trials were also replicated by Montana State University in the following locations in the United States:

Corvallis
Bozeman
Kalispell
Helena

SUMMARY OF THE EMBODIMENTS

The new cultivar is distinguished from other varieties by the following characteristics:

a. Outstanding juice and fresh flavor profile—the pleasant flavor expressed in the invention is characterized by the 'Minaj Shmyrev' lineage and more fitting for the North American market than traditional black currant flavors.

b. Vigorous, upright growth habit, distinguishing 'Nicola' black currant plants from parent variety 'Titania'.

c. High yields—the multiple racemes per bud and number of buds per shoot lend this variety to high flower and fruit counts per plant (FIG. 1 and FIG. 2). In replicated trials in Chilliwack, BC, the variety yielded on average 14 pounds of fruit per plant in comparison to 'Titania', which yielded 15 pounds on average per plant.

d. Even ripening—the mid-season variety, fully cropping a few days before 'Titania', displays even onset of ripening ideal for one-time harvesting of fruit in a commercial setting (FIG. 2).

e. Fruit size—the variety has large fruit even in comparison to other large fruit varieties such as 'Titania'. The average single berry weight for the cultivar is 0.049 ounces compared to 0.035 ounces for 'Titania'. Similarly, the fifty-berry weight is 2.45 ounces compared to 1.7 ounces for 'Titania' on average.

f. Frost tolerance—the fruit of the plant has tolerance to frost as characterized by the Russian plant parent 'Orlovskaya Serenada' during flowering in comparison to 'Titania'. Is tolerant as to temperatures as low as —12 degrees Celsius, not including windchill. Compared with plant parent 'Titania', 'Nicola' is more tolerant of cold conditions at time of flowering; has more upright growth habit, higher yields, significantly larger fruit and outstanding flavor profile. Compared with plant parent 'Orlovskaya Serenada', 'Nicola' flowers 7-9 days later.

g. Disease Resistance: Compared with Ben Alder (U.S. Plant Pat. No. 9,889) and Ben Titania (patent status unknown), 'Nicola' is highly resistant to white pine blister rust and powdery mildew as is its paternal parent 'Titania'.

The cultivar of interest has been asexually reproduced from hardwood cuttings in Courtenay, BC Canada. The area where the plant was discovered is the Comox Valley, BC which has mild weather conditions during most seasons (See FIG. 7).

BRIEF DESCRIPTION OF THE DRAWINGS

The appended photographs demonstrate typical specimens of the new cultivar in color and relative size as true as is reasonably possible.

FIG. 1. Overall growing pattern of the plant. The photograph shows the compact, upright growth pattern of the variety.

FIG. 2. Demonstration of leaf color on the upper side.

FIG. 3. Demonstration of leaf color on the underside, including the venation.

FIG. 4. Demonstration of cane color as well as fruiting structure on the plant.

FIG. 5: Demonstration of the flower density and color on the plants.

FIG. 6: Demonstration of the evenness of color and ripening of the fruit, as well as fruit size in centimeters.

FIG. 7: Weather data for the area where trials were conducted on 'Nicola' showing the low temperatures that the variety was tolerant of FIG. 8: Weather data for the area where trials were conducted on 'Nicola' showing the low temperatures that the variety was tolerant of FIG. 9: Weather data for the area where trials were conducted on 'Nicola' showing the low temperatures that the variety was tolerant of FIG. 10: Weather data for the area where trials were conducted on 'Nicola' showing the low temperatures that the variety was tolerant of FIG. 11: Weather data for the area where trials were conducted on 'Nicola' showing the low temperatures that the variety was tolerant of FIG. 12: Weather data for the area where trials were conducted on 'Nicola' showing the low temperatures that the variety was tolerant of FIG. 13: Weather data for the area where trials were conducted on 'Nicola' showing the low temperatures that the variety was tolerant of FIG. 14: Weather data for the area where trials were conducted on 'Nicola' showing the low temperatures that the variety was tolerant of FIG. 15: Weather data for the area where trials were conducted on 'Nicola' showing the low temperatures that the variety was tolerant of FIG. 16: Demonstration of the inflorescences, including their high density and prominent anthocyanin coloration

DESCRIPTION OF THE PREFERRED EMBODIMENTS

Description of the Cultivar

The following is a detailed description of 3-year-old plants of the new variety as observed at the trial location in Chilliwack, British Columbia, Canada. Colors referenced are described and notated using the Munsell® Color Charts for Plant Tissue standards.

Plant:

*Growth habit*.—Long, upright branches, compact growth, but spreads at time of fruiting due to crop weight making the growth habit high, round.

*Dimensions*.—Average plant height is 73 inches tall and 23 inches in diameter.

*Stems*.—10-12 basal shoots (without pruning); average length of 64 inches and diameter of 0.5 inches. Mottled colored varying between 5 R 3/4 and 2.5 YR 7/4 on the Munsell color chart, with medium roughness.

*Vigor*.—Strong, sturdy shoots usually erect except in over-productive seasons where fruit weight spreads the shoots. Shoots not so brittle as to break under weight.

*Roots*.—Fibrous.

Leaf buds:

*Bud frequency*.—33 buds per stem on average.

*Bud coloration*.—2.5 GY 8/4.

*Bud appearance*.—Acute bud apex tapering shape, 0.625 inches in length and 0.125 inches in diameter on average.

*Bud burst*.—Mar. 15, 2015.

Leaves:

*Leaf coloration*.—Upper leaf 7.5 GY 3/4; lower leaf 5 GY 6/4.

*Leaf appearance*.—Medium glossiness on the upper side and no glossiness on the underside, palmatifid lobed leaf that is cordate in shape at the base and acute at the tip. Leaf margins are serrate.

*Leaf texture*.—Smooth but rugose.

*Leaf venation*.—Dichotomous 5 GY 6/8.

*Leaf configuration*.—In comparison to 'Titania' the base of the leaf is narrower. the terminal lobe is smaller and the rugosity is comparable in severity. See FIG. 4.

*Leaf arrangement*.—Alternating pattern; 28-30 per stem on average.

*Leaf size*.—4.33 inches length and 4.72 inches width on average.

*Petiole coloration*.—5 GY 6/8.

*Petiole dimensions*.—2.874 inches long and 0.157 inches wide on average.

Bract:

*Bract frequency*.—None.

*Bract coloration*.—Not applicable.

*Bract appearance*.—Not applicable.

*Bract texture*.—Not applicable.

Flower bud:

*Bud appearance*.—Narrow acute apex, 0.55 inches in length and 0.2 inches in diameter.

*Bud coloration*.—7.5 GY 8/4.

Flowers:

*Flowering date*.—May 1.

*Flowering period*.—May 1 through May 13.

*Flower coloration*.—5RP 6/10.

*Flower appearance*.—0.5 inches in length and 0.3 inches in diameter, the flowers are bell-shaped to funnel-shaped when in full bloom. No detectable fragrance.

*Flower racemes*.—Long, several per node, frequent.

*Flower frequency*.—Consistently several racemes per bud with 8-12 flowers per raceme.

*Petal frequency*.—5 per flower.

*Petal appearance*.—Linear shape, rounded apex, entire margins, sessile base. 0.3 inches in length and 0.1 inches in diameter, neither surface is waxy, but smooth. More intense anthocyanin coloration compared to the parent variety, 'Titania'.

*Petal texture*.—Slightly downy (both surfaces).

*Sepal to petal frequency*.—1 sepal to 1 petal.

*Sepal appearance*.—Linear shape, rounded apex, entire margins, sessile base. 0.65 inches in length and 0.15 inches in diameter, neither surface is waxy, but smooth.

*Sepal coloration*.—5 R 7/8.

*Anther appearance*.—5 Y 8/8, no dimension data readily available.

*Anther dimensions*.—0.01 inches in length.

*Filament appearance* 2.5 *Y* 8/6.—No dimension data readily available.

*Filament dimensions*.—0.157 inches in length.

*Style appearance*.—Tubular stalk, hairy at base. 2.5 GY 10/8.

*Ovary appearance*.—2.5 GY 8/8, no dimension data readily available.

*Ovary dimensions*.—0.1 inches in diameter.

*Pedicle appearance*.—10 R 7/4, 0.4 inches in length.

*Peduncle appearance*.—2.5 R 8/4, 1.6 inches in length, no data on diameter.

*Peduncle diameter*.—0.078 inches in diameter.

Fruit:

*Size*.—Large sized fruit (notably larger than Ben Alder (U.S. Plant Pat. No. 9,889) and large in comparison to Titania.) The average single berry weight is 0.049 ounces, average diameter is 0.787 inches.

*Color designation*.—5RP 3/2 on ripe fruit.

*Taste*.—Pleasant, sweet, unique, mildly acidic palatable taste.

*Configuration*.—Round.

*Consistency*.—Firm, medium skin thickness, smooth texture, and minimal waxiness.

*Appearance*.—Medium glossiness, black when ripe (5 RP 3/2). Attractive and presented in dense sections with uniform berry size and color within a section. See FIG. 2.

*Fruit ripening*.—Even.

*Yields*.—Multiple racemes per bud, high number of buds per shoot (thus high flower and fruit counts). Yields on average 14 pounds of fruit per plant. Approximately 20 berries per cluster.

*Management and harvesting*.—The variety is suited for machine-harvest as evident by the upright growth and even ripening of fruit. Additionally, the plants are suitable for hand-harvest with the large, firm fruit and multiple tight racemes per bud for quick harvest of many fruit.

*Management and harvesting*.—Suitable for machine harvest due to even ripening and growth habit. Also suitable for hand picking due to easy-to-pick groups of berries (racemes).

*Market*.—Marketable for both commercial and domestic production due to the flexibility in harvest methods (hand or machine). The sweeter, less-acidic taste lends itself for consumption by the North American market both in fresh fruit and processed form. Frost hardiness, white pine blister rust immunity, and mildew resistance allow for robust growing conditions.

*Juice yield*.—48% of berry weight (average of 48 grams of juice extracted from 100 grams of berries using cold press).

*Brix*.—Average 15.7°.

*Seed frequency*.—28 seeds per fruit on average.

*Seed appearance*.—Oval shaped, with tapered ends.

*Seed color designation*.—2.5YR 5/6.

*Seed dimensions*.—0.039 inches.

*Fruit keeping quality*.—high, fruit lasts for approximately 2 weeks in the fridge depending on freshness and ripeness.

Disease and pest resistance: Immune to white pine blister rust (*Cronartium ribicola* Fisch.) in British Columbia (a characteristic of parent plant, 'Titania'). Resistant to powdery mildew and Septoria leaf spot (*Septoria ribis* Desm.).

Resistance to cold: Flowers display frost hardiness compared to its parent plant, 'Titania'. Plants have been exposed to temperatures as low as −12 degrees Celsius, with windchill not taken into account, and suffered no ill effects.

The invention claimed is:

1. I claim a new and distinct variety of Black Currant plant as illustrated and described.

* * * * *

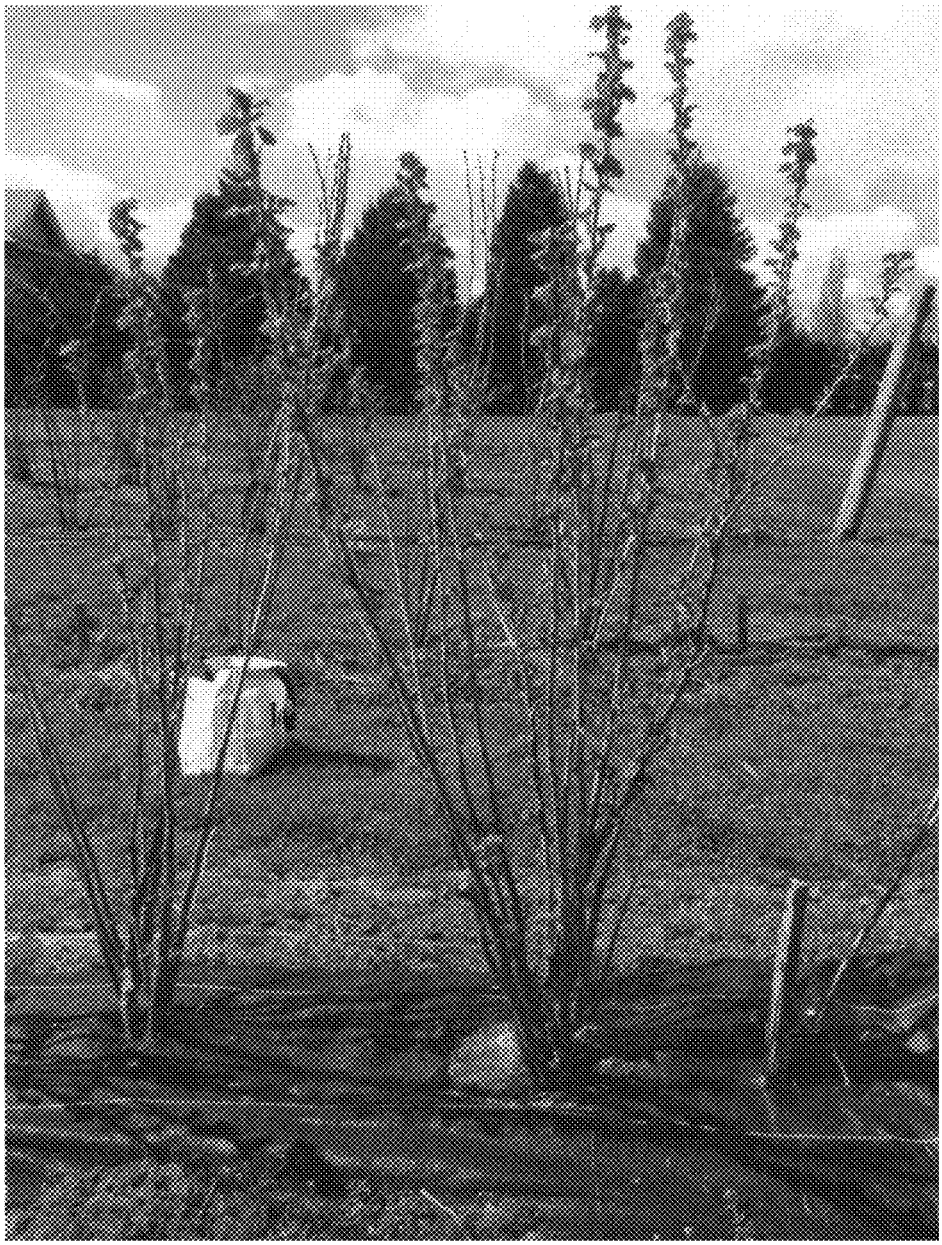
Fig. 1: Overall growing pattern of the plant. The photograph shows the compact, upright growth pattern of the variety.

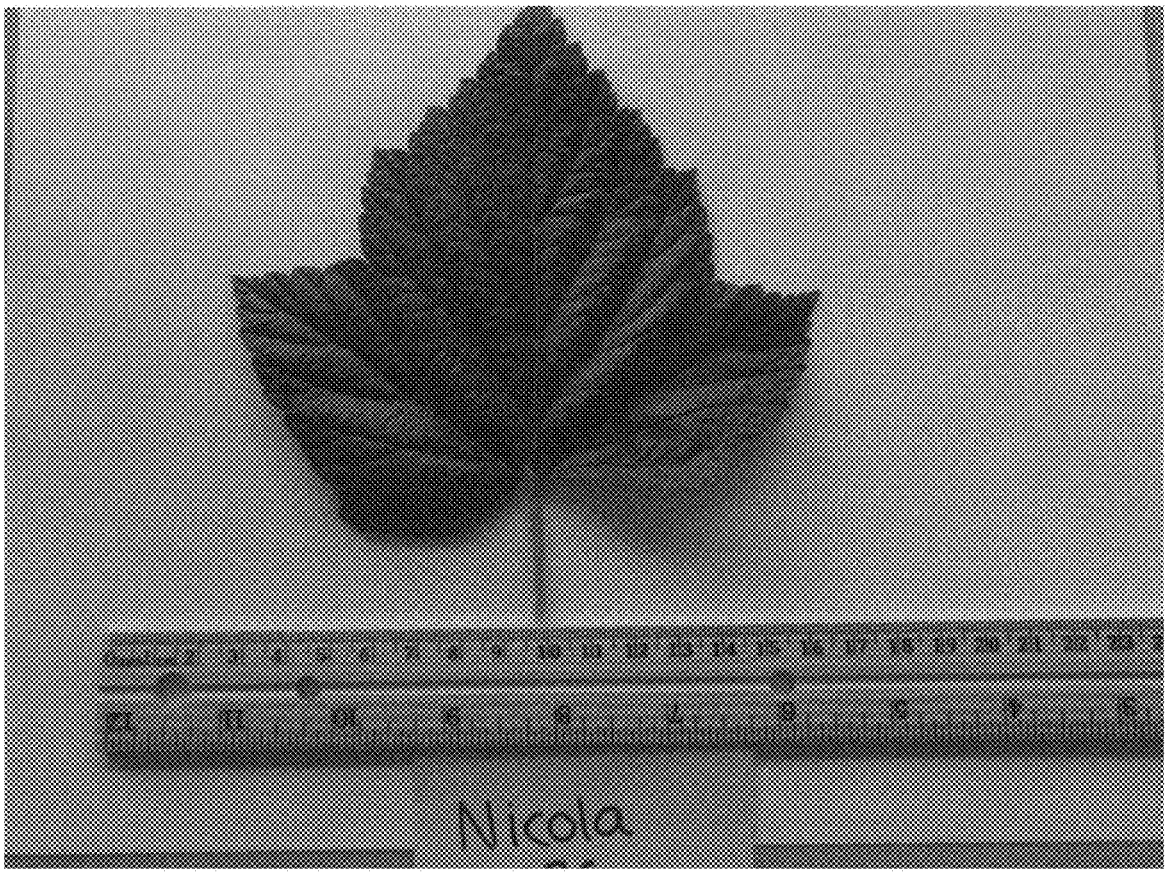
Fig. 2: Demonstration of leaf color on the upper side.

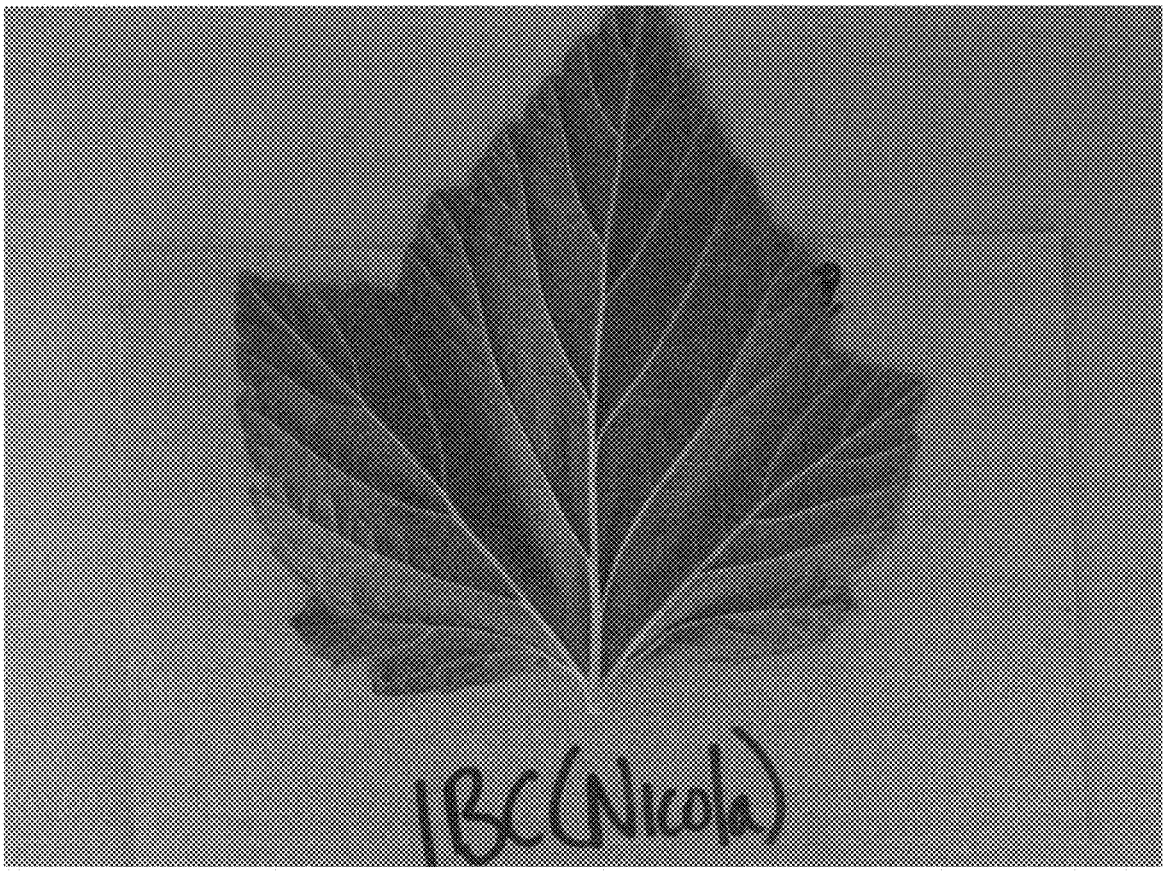
Fig. 3: Demonstration of leaf color on the underside, including the venation.

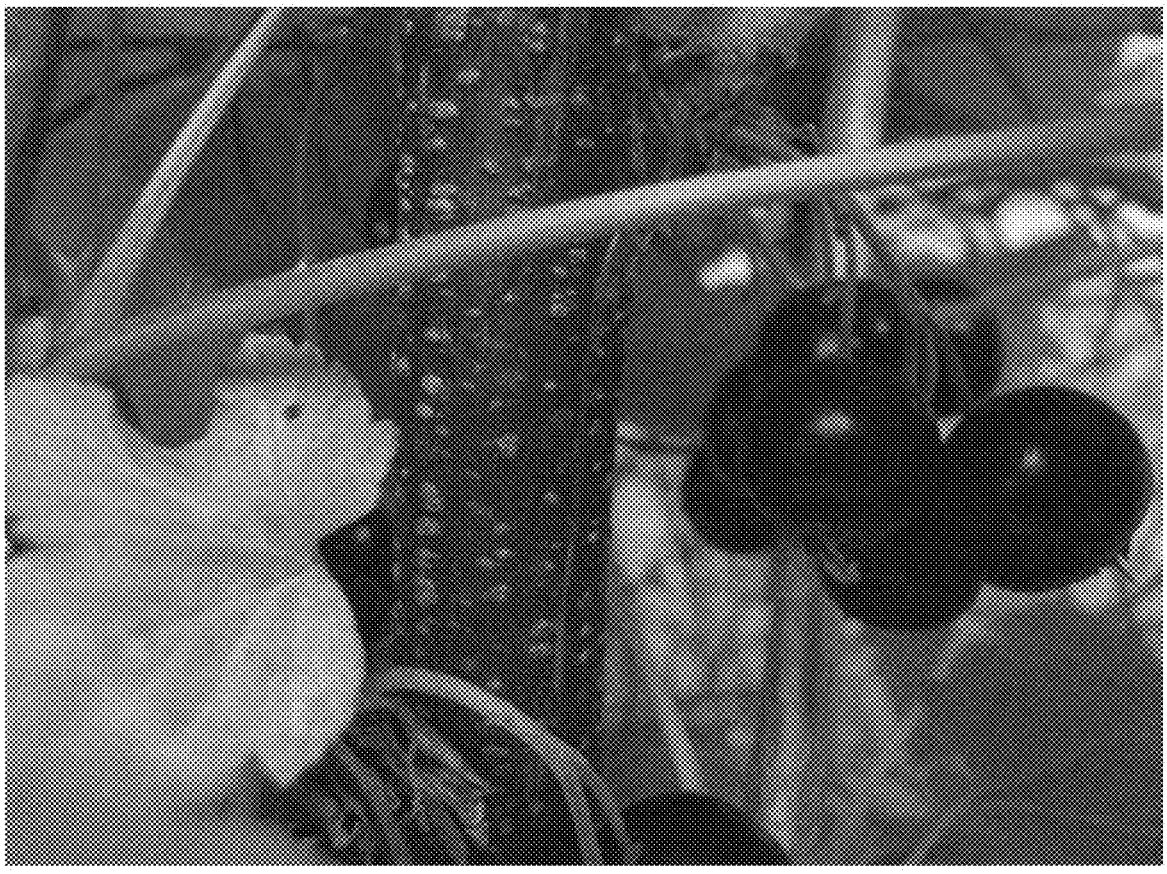
Fig. 4: Demonstration of cane color as well as fruiting structure on the plant.

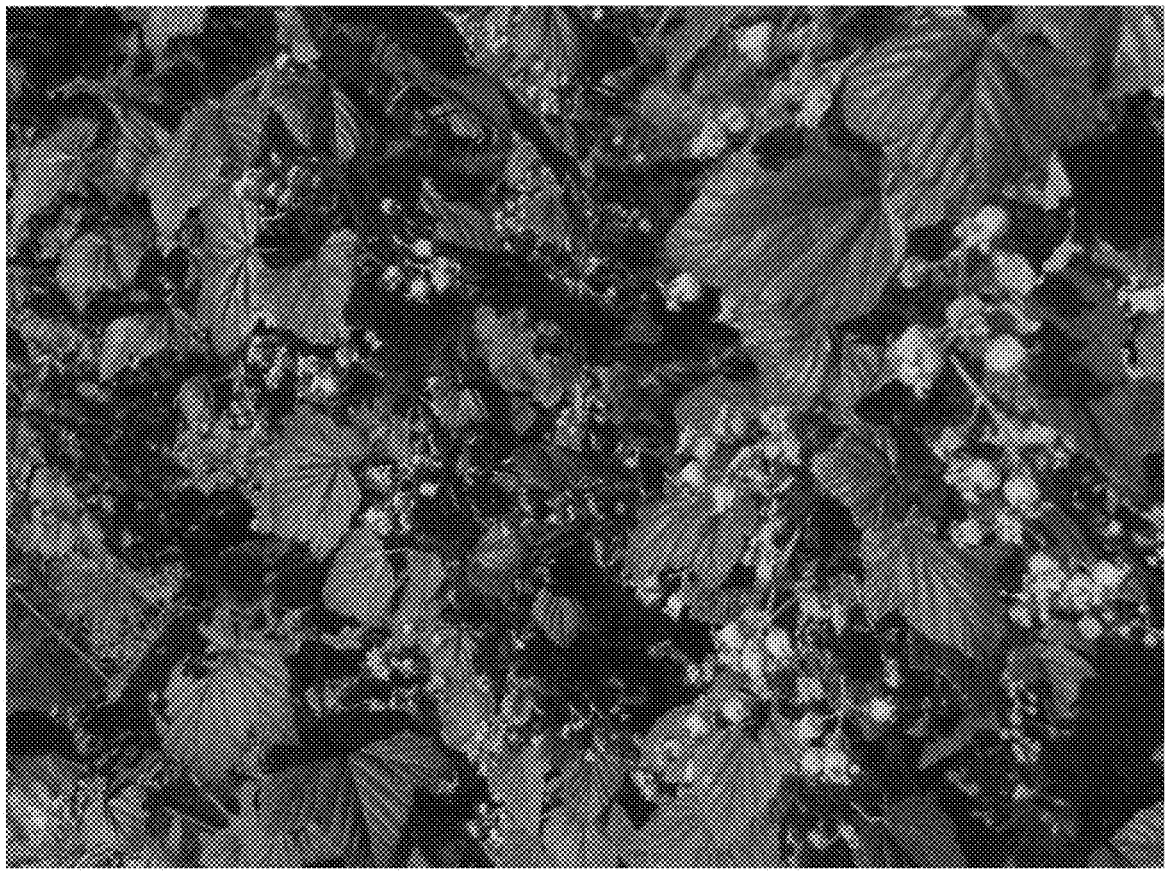
Fig. 5: Demonstration of the flower density and color on the plants.

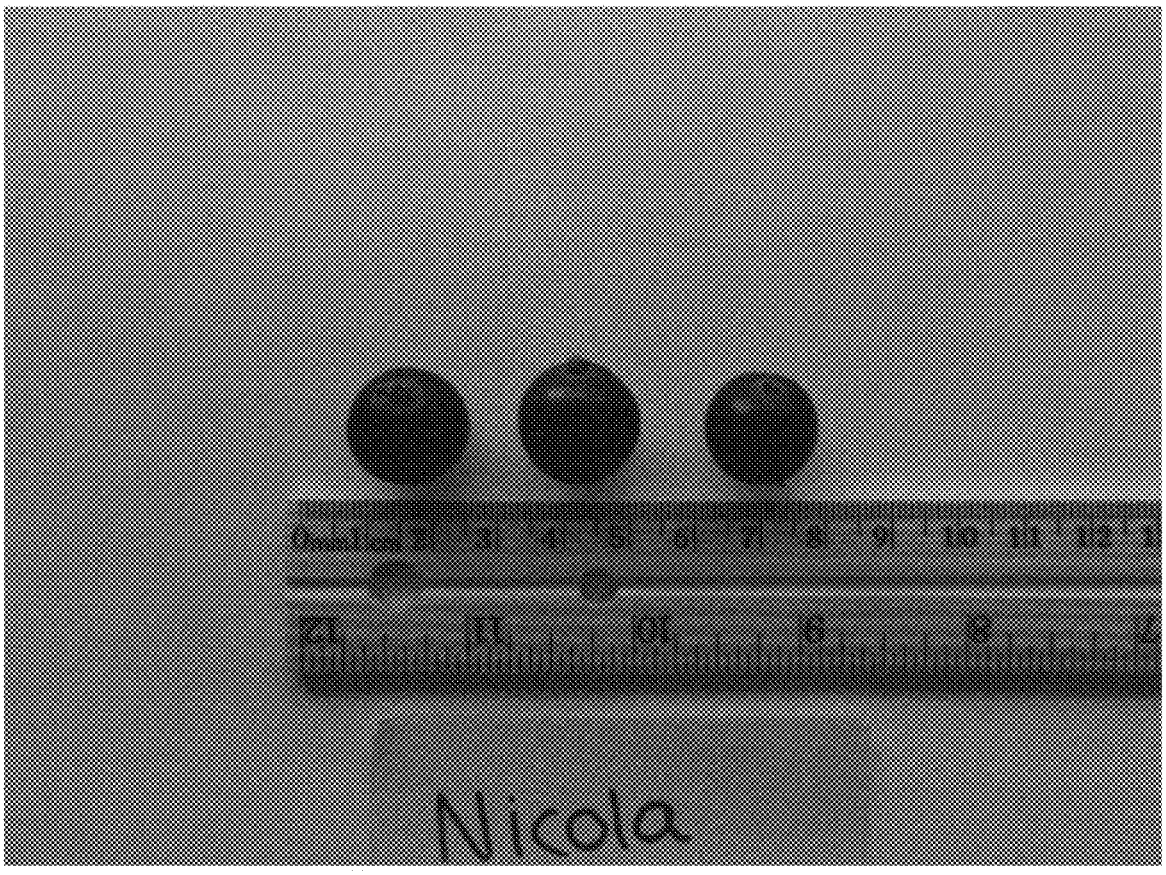
Fig. 6: Demonstration of the evenness of color and ripening of the fruit, as well as fruit size in centimeters.

FIG. 7:
Weather data for the area where trials were conducted on ‘Nicola’ showing the low temperatures that the variety was tolerant of.

Government of Canada Gouvernement du Canada

Home > Environment and natural resources > Weather, Climate and Hazard > Past weather and climate > Historical Data Daily Data Report for December 2018

SUMAS CANAL
BRITISH COLUMBIA
Current Station Operator: CCN

Latitude: 49°06(49.000)' N Longitude: 122°08(35.004)' W Elevation: 9.00 m
Climate ID: 1107785 WMO ID: TC ID:

| DAY | Max Temp °C | Min Temp °C | Mean Temp °C | Heat Deg Days | Cool Deg Days | Total Rain mm | Total Snow cm | Total Precip mm | Snow on Grnd cm | Dir of Max Gust 10's deg | Spd of Max Gust km/h |
|---|---|---|---|---|---|---|---|---|---|---|---|
| 01 | | | | | | | | | | | |
| 02 ‡ | 9.0 | M | M | M | M | 3.0 | 0.0 | 3.0 | | | |
| 03 ‡ | 7.0 | 2.0 | 4.5 | 13.5 | 0.0 | 0.0 | 0.0 | 0.0 | 0 | | |
| 04 ‡ | M | 0.5 | M | M | M | | | | 0 | | |
| 05 ‡ | 5.0 | M | M | M | M | 0.0 | 0.0 | 0.0 | | | |
| 06 ‡ | 4.0 | 0.0 | 2.0 | 16.0 | 0.0 | 0.0 | 0.0 | 0.0 | 0 | | |

| DAY | Max Temp °C (M) | Min Temp °C (M) | Mean Temp °C (M) | Heat Deg Days (M) | Cool Deg Days (M) | Total Rain mm (M) | Total Snow cm (M) | Total Precip mm (M) | Snow on Grnd cm (M) | Dir of Max Gust 10's deg | Spd of Max Gust km/h (M) |
|---|---|---|---|---|---|---|---|---|---|---|---|
| 07 : | M | -1.0 | M | M | M | | | | 0 | | |
| 08 | | | | | | | | | | | |
| 09 : | 8.0 | M | M | M | M | 25.6 | 0.0 | 25.6 | | | |
| 10 : | 8.0 | 1.0 | 4.5 | 13.5 | 0.0 | 15.6 | 0.0 | 15.6 | 0 | | |
| 11 : | 11.0 | 4.0 | 7.5 | 10.5 | 0.0 | 25.0 | 0.0 | 25.0 | 0 | | |
| 12 : | 10.0 | 4.0 | 7.0 | 11.0 | 0.0 | 35.6 | 0.0 | 35.6 | 0 | | |
| 13 : | 10.5 | 4.0 | 7.3 | 10.7 | 0.0 | 11.0 | 0.0 | 11.0 | 0 | | |
| 14 : | M | 4.0 | M | M | M | | | | 0 | | |
| 15 | | | | | | | | | | | |
| 16 | | | | | | | | | | | |
| 17 : | 14.5 | M | M | M | M | 42.0 | 0.0 | 42.0 | | | |
| 18 : | M | 4.0 | M | M | M | | | | 0 | | |
| 19 | | | | | | | | | | | |
| 20 : | 16.0 | M | M | M | M | 11.0 | 0.0 | 11.0 | | | |
| 21 : | M | 2.5 | M | M | M | | | | 0 | | |
| 22 | | | | | | | | | | | |
| 23 : | 5.5 | M | M | M | M | 25.0 | 0.0 | 25.0 | | | |
| 24 : | M | -6.0 | M | M | M | | | | 0 | | |
| 25 | | | | | | | | | | | |
| 26 : | 7.5 | M | M | M | M | 8.0 | 0.0 | 8.0 | | | |

Fig. 8: Weather data for the area where trials were conducted on ‘Nicola’ showing the low temperatures that the variety was tolerant of.

| DAY | Max Temp °C ✓ | Min Temp °C ✓ | Mean Temp °C ✓ | Heat Deg Days ✓ | Cool Deg Days ✓ | Total Rain mm ✓ | Total Snow cm ✓ | Total Precip mm ✓ | Snow on Grnd cm ✓ | Dir of Max Gust 10's deg | Spd of Max Gust km/h ✓ |
|---|---|---|---|---|---|---|---|---|---|---|---|
| 27 ‡ | 4.5 | 1.0 | 2.8 | 15.2 | 0.0 | 2.0 | 0.0 | 2.0 | 0 | | |
| 28 ‡ | M | -4.5 | M | M | M | | | | 0 | | |
| 29 | | | | | | | | | | | |
| 30 ‡ | 12.5 | M | M | M | M | 39.0 | 0.0 | 39.0 | | | |
| 31 ‡ | M | -6.0 | M | M | M | | | | 0 | | |
| Sum | | | | 90.4^ | 0.0^ | 243.8^ | 0.0^ | 243.8^ | | | |
| Avg | 8.9^ | 0.6^ | 5.1^ | | | | | | | | |
| Xtrm | 16.0^ | -6.0^ | | | | | | | | | |

Summary, average and extreme values are based on the data above.

Legend

- A = Accumulated
- C = Precipitation occurred, amount uncertain
- E = Estimated
- F = Accumulated and estimated
- L = Precipitation may or may not have occurred
- M = Missing
- N = Temperature missing but known to be > 0
- S = More than one occurrence
- T = Trace
- Y = Temperature missing but known to be < 0
- [empty] = Indicates an unobserved value
- ^ = The value displayed is based on incomplete data
- ‡ = Data that is not subject to review by the National Climate Archives

Date modified:

2020-09-17

Fig. 9: Weather data for the area where trials were conducted on ‘Nicola’ showing the low temperatures that the variety was tolerant of.

Government of Canada Gouvernement du Canada

Home > Environment and natural resources > Weather, Climate and Hazard > Past weather and climate > Historical Data Daily Data Report for January 2020

SUMAS CANAL
BRITISH COLUMBIA
Current Station Operator: CCN

| | | | | | | |
|---|---|---|---|---|---|---|
| Latitude: | 49°06'48.008" N | Longitude: | 122°06'35.004" W | Elevation: | 9.00 m | |
| Climate ID: | 1107785 | WMO ID: | | TC ID: | | |

| DAY | Max Temp °C | Min Temp °C | Mean Temp °C | Heat Deg Days | Cool Deg Days | Total Rain mm | Total Snow cm | Total Precip mm | Snow on Grnd cm | Dir of Max Gust 10's deg | Spd of Max Gust km/h |
|---|---|---|---|---|---|---|---|---|---|---|---|
| 01 ‡ | 13.0 | M | M | M | M | 34.0 | 0.0 | 34.0 | | | |
| 02 ‡ | M | 4.5 | M | M | M | | | | 0 | | |
| 03 | | | | | | | | | | | |
| 04 | | | | | | | | | | | |
| 05 ‡ | 16.5 | M | M | M | M | 34.0 | 0.0 | 34.0 | | | |
| 06 ‡ | 5.5 | 1.0 | 3.3 | 14.7 | 0.0 | 64.0 | 0.0 | 64.0 | 0 | | |

Fig. 10: Weather data for the area where trials were conducted on 'Nicola' showing the low temperatures that the variety was tolerant of.

| DAY | Max Temp °C | Min Temp °C | Mean Temp °C | Heat Deg Days | Cool Deg Days | Total Rain mm | Total Snow cm | Total Precip mm | Snow on Grnd cm | Dir of Max Gust 10's deg | Spd of Max Gust km/h |
|---|---|---|---|---|---|---|---|---|---|---|---|
| 07 | 13.0 | 0.5 | 5.3 | 12.7 | 0.0 | 18.6 | 0.0 | 18.6 | 0 | | |
| 08 | 5.5 | 3.0 | 4.3 | 13.7 | 0.0 | 4.0 | 0.0 | 4.0 | 0 | | |
| 09 | 5.5 | 1.5 | 3.5 | 14.5 | 0.0 | 0.6 | 1.0 | 1.6 | 0 | | |
| 10 | M | 0.0 | M | M | M | | | | 0 | | |
| 11 | | | | | | | | | | | |
| 12 | 5.5 | M | M | M | M | 0.0 | 9.0 | 9.0 | | | |
| 13 | -8.0 | -10.0 | -9.0 | 27.0 | 0.0 | 0.0 | 0.0 | 0.0 | 0 | | |
| 14 | -10.0 | -11.0 | -10.5 | 28.5 | 0.0 | 0.0 | 12.0 | 12.0 | 0 | | |
| 15 | M | -12.0 | M | M | M | | | | 0 | | |
| 16 | -4.5 | M | M | M | M | 0.0 | 7.0 | 7.0 | | | |
| 17 | M | -9.0 | M | M | M | | | | 0 | | |
| 18 | | | | | | | | | | | |
| 19 | 8.0 | M | M | M | M | 5.0 | 0.0 | 5.0 | | | |
| 20 | 7.5 | -8.0 | -0.3 | 18.3 | 0.0 | 4.0 | 0.0 | 4.0 | 0 | | |
| 21 | 9.5 | 4.0 | 6.8 | 11.2 | 0.0 | 16.6 | 0.0 | 16.6 | 0 | | |
| 22 | 6.0 | 3.5 | 4.8 | 13.2 | 0.0 | 18.0 | 0.0 | 18.0 | 0 | | |
| 23 | M | 4.0 | M | M | M | | | | 0 | | |
| 24 | | | | | | | | | | | |
| 25 | | | | | | | | | | | |
| 26 | 12.5 | M | M | M | M | 19.0 | 0.0 | 19.0 | | | |

Fig. 11: Weather data for the area where trials were conducted on 'Nicola' showing the low temperatures that the variety was tolerant of.

| DAY | Max Temp °C | Min Temp °C | Mean Temp °C | Heat Deg Days | Cool Deg Days | Total Rain mm | Total Snow cm | Total Precip mm | Snow on Grnd cm | Dir of Max Gust 10's deg | Spd of Max Gust km/h |
|---|---|---|---|---|---|---|---|---|---|---|---|
| 27 † | 10.5 | 4.0 | 7.3 | 10.7 | 0.0 | 9.0 | 0.0 | 9.0 | 0 | | |
| 28 † | 7.0 | 4.5 | 5.8 | 12.2 | 0.0 | 9.8 | 0.0 | 9.8 | 0 | | |
| 29 † | 10.5 | 4.5 | 7.5 | 10.5 | 0.0 | 13.0 | 0.0 | 13.0 | 0 | | |
| 30 † | 8.0 | 1.0 | 4.5 | 13.5 | 0.0 | 36.6 | 0.0 | 36.6 | 0 | | |
| 31 † | 15.0 | 4.5 | 9.8 | 8.2 | 0.0 | 62.0 | 0.0 | 62.0 | 0 | | |
| Sum | | | | 208.9^ | 0.0^ | 348.2^ | 29.0^ | 377.2^ | | | |
| Avg | 8.7^ | -0.5^ | 3.1^ | | | | | | | | |
| Xtrm | 16.5^ | -12.0^ | | | | | | | | | |

Summary, average and extreme values are based on the data above.

Legend

- A = Accumulated
- C = Precipitation occurred, amount uncertain
- E = Estimated
- F = Accumulated and estimated
- L = Precipitation may or may not have occurred
- M = Missing
- N = Temperature missing but known to be > 0
- S = More than one occurrence
- T = Trace
- Y = Temperature missing but known to be < 0
- [empty] = Indicates an unobserved value
- ^ = The value displayed is based on incomplete data
- † = Data that is not subject to review by the National Climate Archives

Date modified:

2020-09-17

Fig. 12: Weather data for the area where trials were conducted on 'Nicola' showing the low temperatures that the variety was tolerant of.

Government of Canada Gouvernement du Canada

Home > Environment and natural resources > Weather, Climate and Hazard > Past weather and climate > Historical Data Daily Data Report for February 2019

SUMAS CANAL
BRITISH COLUMBIA
Current Station Operator: CCN

Latitude: 49°06'48.008" N Longitude: 122°06'35.004" W Elevation: 9.00 m

Climate ID: 1107785 WMO ID: TC ID:

| DAY | Max Temp °C | Min Temp °C | Mean Temp °C | Heat Deg Days | Cool Deg Days | Total Rain mm | Total Snow cm | Total Precip mm | Snow on Grnd cm | Dir of Max Gust 10's deg | Spd of Max Gust km/h |
|---|---|---|---|---|---|---|---|---|---|---|---|
| 01 | | | | | | | | | | | |
| 02 | | | | | | | | | | | |
| 03 ‡ | 9.0 | M | M | M | M | 0.0 | 0.0 | 0.0 | | | |
| 04 ‡ | -3.5 | -9.0 | -6.3 | 24.3 | 0.0 | 0.0 | 0.0 | 0.0 | 0 | | |
| 05 ‡ | -1.0 | -9.0 | -5.0 | 23.0 | 0.0 | 0.0 | 0.0 | 0.0 | 0 | | |
| 06 ‡ | 2.0 | -8.5 | -3.3 | 21.3 | 0.0 | 0.0 | 0.0 | 0.0 | 0 | | |

Fig. 13: Weather data for the area where trials were conducted on 'Nicola' showing the low temperatures that the variety was tolerant of.

| DAY | Max Temp °C | Min Temp °C | Mean Temp °C | Heat Deg Days | Cool Deg Days | Total Rain mm | Total Snow cm | Total Precip mm | Snow on Grnd cm | Dir of Max Gust 10's deg | Spd of Max Gust km/h |
|---|---|---|---|---|---|---|---|---|---|---|---|
| 07 † | 2.0 | -5.0 | -1.5 | 19.5 | 0.0 | 0.0 | 0.0 | 0.0 | 0 | | |
| 08 † | M | -4.0 | M | M | M | | | | 0 | | |
| 09 | | | | | | | | | | | |
| 10 | | | | | | | | | | | |
| 11 † | -3.0 | M | M | M | M | 0.0 | 6.0 | 6.0 | | | |
| 12 † | M | -5.0 | M | M | M | | | | 0 | | |
| 13 † | 1.0 | M | M | M | M | 0.0 | 0.0 | 0.0 | | | |
| 14 † | 2.5 | -4.0 | -0.8 | 18.8 | 0.0 | 0.0 | 2.0 | 2.0 | 0 | | |
| 15 † | M | -1.0 | M | M | M | | | | 0 | | |
| 16 | | | | | | | | | | | |
| 17 | | | | | | | | | | | |
| 18 † | 7.0 | M | M | M | M | 0.0 | 6.0 | 6.0 | | | |
| 19 † | 3.5 | -2.0 | 0.8 | 17.2 | 0.0 | 0.0 | 0.0 | 0.0 | 0 | | |
| 20 † | 6.0 | -7.0 | -0.5 | 18.5 | 0.0 | 0.0 | 0.0 | 0.0 | 0 | | |
| 21 † | 6.0 | -1.0 | 2.5 | 15.5 | 0.0 | 0.0 | 3.0 | 3.0 | 0 | | |
| 22 † | M | -1.0 | M | M | M | | | | 0 | | |
| 23 | | | | | | | | | | | |
| 24 † | 7.0 | M | M | M | M | 0.0 | 0.0 | 0.0 | | | |
| 25 † | 3.0 | -0.5 | 1.3 | 16.7 | 0.0 | 0.0 | 0.0 | 0.0 | 0 | | |
| 26 † | M | -4.0 | M | M | M | | | | 0 | | |

Fig. 14: Weather data for the area where trials were conducted on 'Nicola' showing the low temperatures that the variety was tolerant of.

| DAY | Max Temp °C | Min Temp °C | Mean Temp °C | Heat Deg Days | Cool Deg Days | Total Rain mm | Total Snow cm | Total Precip mm | Snow on Grnd cm | Dir of Max Gust 10's deg | Spd of Max Gust km/h |
|---|---|---|---|---|---|---|---|---|---|---|---|
| 27 † | 6.0 | M | M | M | M | 0.0 | 0.0 | 0.0 | | | |
| 28 † | M | -1.0 | M | M | M | | | | 0 | | |
| Sum | | | | 174.8^ | 0.0^ | 0.0^ | 17.0^ | 17.0^ | | | |
| Avg | 3.2^ | -4.1^ | -1.4^ | | | | | | | | |
| Xtrm | 9.0^ | -9.0^ | | | | | | | | | |

Summary, average and extreme values are based on the data above.

Legend

- A = Accumulated
- C = Precipitation occurred, amount uncertain
- E = Estimated
- F = Accumulated and estimated
- L = Precipitation may or may not have occurred
- M = Missing
- N = Temperature missing but known to be > 0
- S = More than one occurrence
- T = Trace
- Y = Temperature missing but known to be < 0
- [empty] = Indicates an unofficial value
- ^ = The value displayed is based on incomplete data
- † = Data that is not subject to review by the National Climate Archives Date modified:
2020-09-17

Fig. 15: Weather data for the area where trials were conducted on 'Nicola' showing the low temperatures that the variety was tolerant of.

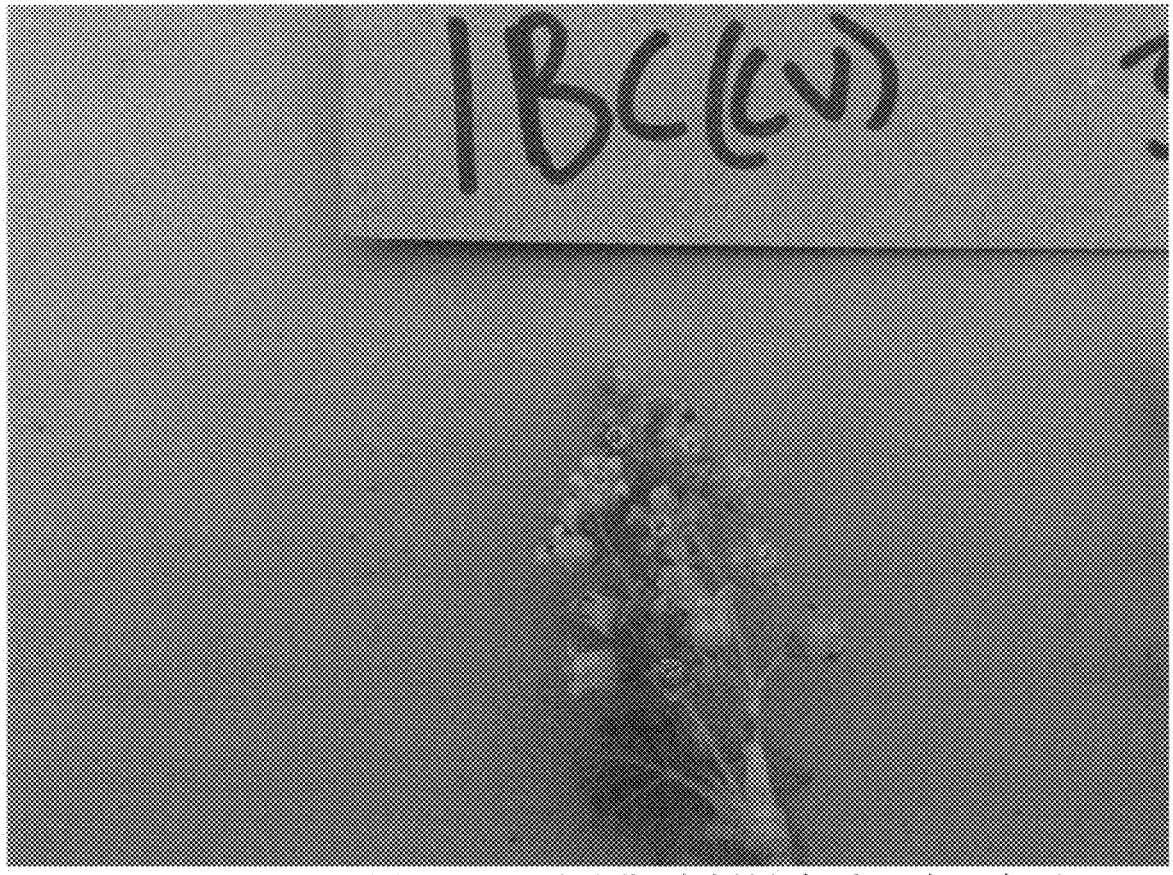
Fig. 16: Demonstration of the inflorescences, including their high density and prominent anthocyanin coloration.